United States Patent [19]
Jepson et al.

[11] Patent Number: 5,719,329
[45] Date of Patent: Feb. 17, 1998

[54] ULTRASONIC MEASURING SYSTEM AND METHOD OF OPERATION

[75] Inventors: William Paul Jepson; Madan Gopal, both of Athens, Ohio

[73] Assignee: Ohio University, Athens, Ohio

[21] Appl. No.: 768,994

[22] Filed: Dec. 18, 1996

Related U.S. Application Data

[60] Provisional application No. 60/009,288, Dec. 28, 1995.

[51] Int. Cl.[6] .......................... G01N 29/02; G01N 29/28; G01F 1/74
[52] U.S. Cl. .................... 73/61.49; 73/597; 73/861.04
[58] Field of Search ........................... 73/597, 290 V, 73/19.03, 54.41, 195, 198, 861.04, 861.18, 861.25, 861.26, 861.27, 861.28, 861.29, 861.31, 622; 364/510, 506

[56] References Cited

U.S. PATENT DOCUMENTS

| | | | |
|---|---|---|---|
| H608 | 3/1989 | Goolsby | 73/290 V |
| 3,940,985 | 3/1976 | Wyler | 73/194 A |
| 4,109,523 | 8/1978 | Teyssandier | 73/194 A |
| 4,118,983 | 10/1978 | Brazhnikov | 73/290 V |
| 4,317,178 | 2/1982 | Head | 73/861 |
| 4,402,230 | 9/1983 | Raptis | 73/861.04 |
| 4,523,468 | 6/1985 | Derkacs et al. | 73/598 |
| 4,545,244 | 10/1985 | Yasuda et al. | 73/195 |
| 4,628,725 | 12/1986 | Gouilloud et al. | 73/19 |
| 4,646,575 | 3/1987 | O'Hair et al. | 73/861.31 |
| 5,228,337 | 7/1993 | Lowell et al. | 73/861.28 |
| 5,473,934 | 12/1995 | Cobb | 73/61.49 |
| 5,589,642 | 12/1996 | Agar et al. | 73/861.04 |
| 5,594,181 | 1/1997 | Stange | 73/861.28 |
| 5,597,962 | 1/1997 | Hastings et al. | 73/861.29 |
| 5,600,073 | 2/1997 | Hill | 73/861.04 |

OTHER PUBLICATIONS

Michael J. Riezenman, "Ultrasonic Meters Go With the Flow", Mechanical Engineering, Sep. 1989, pp. 74–77.

Roger N. Blais, Assoc. Professor—Dept. of Engineering Physics, The University of Tulsa; "Void Fraction Instrumentation System on Three Inch Two-Phase Flowline", ISA, 1982; pp. 883–889.

J. E. Laurinat, T. J. Hanratty and W. P. Jepson; "Film Thickness Distribution for Gas-Liquid Annular Flow in a Horizontal Pipe", PCH PhysicoChemical Hydrodynamics, vol. 6, No. 1/2, pp. 179–195, 1985.

S.L. Moriss and A.D. Hill, U. of Texas, "Measurement of Velocity Profiles in Upwards Oil/Water Flow Using Ultrasonic Doppler Velocimetry"; SPE 22766, 1991 SPE Annl. Tech. Conf., pp. 65–79.

Y.A. Hassan, T.K. Blanchat, C.H. Seeley Jr. and R.E. Canaan, "Simultaneous Velocity Measurements of Both Components of a Two-Phase Flow Using Particle Image Velocimetry"; Int. J. Multiphase Flow, vol. 18, No. 3, pp. 371–395, 1992.

(List continued on next page.)

Primary Examiner—Hezron E. Williams
Assistant Examiner—Rose M. Miller
Attorney, Agent, or Firm—Killworth, Gottman, Hagan & Schaeff, L.L.P.

[57] ABSTRACT

An ultrasonic measuring system is provided including a plurality of upstream and downstream ultrasonic transducers coupled to a multiflow pipeline and positioned along first and second cross sectional portions of the multiflow pipeline. A transducer control system is coupled to the upstream and downstream ultrasonic transducers for selective activation of the transducers. In one embodiment, the ultrasonic measuring system is utilized to determine a flow velocity of a selected fluid in a multiflow pipeline by generating and detecting velocimetric ultrasonic pulses in the selected fluid. In another embodiment, the ultrasonic measuring system is utilized to determine film heights of fluids flowing within the pipeline.

19 Claims, 4 Drawing Sheets

OTHER PUBLICATIONS

Joseph Baumoel, President of Controlotron, "Comparative Advantages of Clamp–On Transmit–Time Ultrasonic Flowmeters Over Conventional Intrusive Flowmeters", © 1993 All Rights Reserved, pp. 1–4.

Report by Victoria Thomas entitled "New Technology Revolutionises Gas Metering", Gas Engineering & Management, May 1994, pp. 115–116.

W.J. Priddy, "Field Trials of Multiphase Metering Systems at Prudhoe Bay", Alaska, SPE 28514, Presentation at 69th Annual Tech. Conference, Sep. 25–28, 1994.

Michael Rogi, "Ultrasonic Measurement for Mainline Applications", Gas Industries, Nov. 1994; pp. 19–20.

S. Neogi, A. Lee & W.P. Jepson, "A Model for Multiphase (Gas–Water–Oil) Stratified Flow in Horizontal Pipelines", SPE 28799, presentation at SPE Asia Pacific Oil & Gas Conference, Nov., 1944; pp. 553–560.

"Adaptive Phase Doppler Velocimeter Gives Particle Size and Velocity", vol. 4, Issue 1, TSI Incorporated, Fluid Mechanics Instrument Division, p. 1 (no date available).

J.K. Sidney, Dr. J. Coulthard and Dr. R.P. Keech, "Cross Correlation Flow Measurements in Two–Phase Air–Water Mixtures", 18 pages.

V. Kefer, W. Kratzer, B. Brand and W. Kastner, "Measurement Techniques for Two–Phase Flow—Survey and Development of a New Mass Flow Meter", 24 pages.

Dr. B.C. Millington and N.W. King, "Development of a Jet Mixer/Turbine Meter Package for Metering Gas–Liquid Mixtures", 24 pages.

Dr. Ing U. Wernekinck, "Installation for Calibrating, Under Operating Conditions of Turbine Gas Meters", 26 pages.

Dr. T. L. Jones, "Gas Flow Rate Measurement Using the Helium Dilution Technique", 19 pages.

Joshi, Shrinivas G.; Jin, Yu USA; Abstract of "Application of a Surface–Acoustic–Wave Device for Measurement of Liquid Flow Rate", IEEE Transactions on Ultrasonics, Ferroelectrics, and Frequency Control, vol. 37, Sep. 1990, pp. 475–477 (abstract only).

S.L. Morriss, Abstract of "Ultrasonic Imaging and Velocimetry in Two–Phase Pipe Flow", American Society of Mechanical Engineers (Paper), published by ASME, 1990; presentation at Energy–Sources Technology Conference and Exhibition held Jan. 14–18, 1990 (abstract only).

S. G. Foster, P.M. Embree, W. D. O'Brien, Abstract of "Flow Felocity Profile via Time–Domain Correlation: Error Control", vol. 37, May 1990, pp. 164–175 (abstract only).

G. A. Jackson, J. R. Gibson and R. Holmes, Abstract of "Three–Path Ultrasonic Flow Meter with Fluid Velocity Profile Identification", Measurement Science & Technology, vol. 2, No. 7, Jul., 1991, pp. 635–642 (abstract only).

Steve Brown, Abstract of "Level Measurement. Reaching New Peaks?" Process Engineering (London), vol. 71, No. 7, Jul. 1990, pp. 37–38 (abstract only).

Author: Anonymous, Abstract of "Oklahoma Natural Evaluates Multipath Ultrasonic Meter", Gas Industries (Park Ridge, IL), 39, Nov., 1994, pp. 17–18 (abstract only).

Author: Anonymous; Abstract of "Ultrasonic Flow Meters", Pipeline and Gas Journal, vol. 217, No. 10, Oct. 1990.

ULTRASONIC MEASURING SYSTEM AND METHOD OF OPERATION

CROSS REFERENCE TO RELATED APPLICATIONS

This application claims the benefit of U.S. Provisional Application No. 60/009,288, filed Dec. 28, 1995.

BACKGROUND OF THE INVENTION

The present invention relates to multiflow pipelines wherein multiple fluid phases flow through a single pipeline and, in particular, to the determination of the flow rates and film heights of the different fluid phases flowing within a pipeline.

In a variety of industrial and experimental applications, it is necessary to monitor the flow of a collection of fluids in a pipeline. For example, in the oil and gas industry, three distinct fluid phases, i.e., oil, water, and gas, exist in horizontal pipelines. Multiphase flow metering, wherein the velocity of each fluid phase flowing within a pipeline is metered, presents the potential for valuable insight into the analysis of multiphase pipeline stress and multiphase pipeline system design. Many of the conventional multiphase flow metering systems do not provide an accurate indication of the flow velocity of each fluid phase flowing within a pipeline because of inherent limitations in their methodology. Further, other conventional systems are prohibitively difficult to install or incorporate intrusive metering arrangements requiring interruption or alteration of the multiphase flow. Finally, many conventional systems are merely compatible with a limited range of pipeline designs and, accordingly, have limited utility.

Accordingly, there is a need for a multiphase flow metering system and method incorporating a non-intrusive, versatile, accurate, readily installable, and cost effective multiphase fluid metering design.

SUMMARY OF THE INVENTION

This need is met by the present invention wherein a method and an apparatus for the determination of fluid film heights of each fluid flowing within a multiflow pipeline and the generation and detection of velocimetric ultrasonic pulses within a selected fluid within the pipeline. By a "multiflow pipeline" we mean a pipeline through which multiple fluid phases flow.

In accordance with one embodiment of the present invention, an ultrasonic measuring system is provided comprising: a plurality of upstream ultrasonic transducers coupled to a multiflow pipeline and positioned along a first cross sectional portion of a multiflow pipeline; a plurality of downstream ultrasonic transducers coupled to a multiflow pipeline and positioned along a second cross sectional portion of the multiflow pipeline; and a transducer control system coupled to the plurality of upstream ultrasonic transducers and the plurality of downstream ultrasonic transducers. The first and second cross sectional portions are preferably substantially perpendicular to a flow axis of the pipeline.

The transducer control system may comprise a programmable controller and a signal multiplexer, and the signal multiplexer preferably includes signal outputs coupled to respective ones of the plurality of upstream and downstream ultrasonic transducers. The transducer control system is preferably operative to cause ultrasonic signals to be generated at any one or more of the plurality of upstream and downstream ultrasonic transducers and detected at any one or more of the plurality of upstream and downstream ultrasonic transducers.

The transducer control system of the present invention is preferably operative to determine a film height of a selected fluid within the multiflow pipeline or to determine film heights of each of a plurality of fluids present within the multiflow pipeline by generating and detecting at least one ultrasonic pulse in a single cross section of the pipeline. Ultrasonic signals may be generated and detected at a lowermost portion of a single cross section of the multiflow pipeline. First and second reflected ultrasonic signals may be detected at the lowermost portion.

The transducer control system may be operative to generate and detect ultrasonic pulses within a single fluid selected from a plurality of fluids present within the multiflow pipeline and to determine a flow velocity of a single fluid selected from a plurality of fluids present within the multiflow pipeline by generating and detecting ultrasonic pulses within the single fluid. Preferably, the ultrasonic pulse is generated in a first cross section of the pipeline and detected in another cross section of the pipeline.

In accordance with another embodiment of the present invention, a method of operating an ultrasonic measuring system is provided comprising the steps of: determining a first ultrasonic absorption coefficient corresponding to a first pipeline fluid occupying a first flow portion of a multiflow pipeline; determining a first ultrasonic propagation factor corresponding to a first interface between the first pipeline fluid and a second pipeline fluid occupying a second flow portion of the pipeline; generating an ultrasonic pulse at a lowermost portion of a cross section of the pipeline; detecting a first reflected ultrasonic pulse at the lowermost portion, the first reflected ultrasonic pulse being reflected from the interface between the first pipeline fluid and the second pipeline fluid; and calculating a first pipeline fluid film height based on the generated ultrasonic pulse, the first ultrasonic absorption coefficient, the first ultrasonic propagation factor, and the first reflected ultrasonic pulse.

The cross sectional boundaries of the first flow portion may be determined based on the first pipeline fluid film height. A set of one or more velocimetric ultrasonic pulses may be generated and detected within the cross sectional boundaries of the first flow portion. The flow velocity of the first pipeline fluid may be calculated based on the generated set of velocimetric ultrasonic pulses and the detected set of velocimetric ultrasonic pulses.

Similarly, the cross sectional boundaries of the second flow portion may be determined based on the first pipeline fluid film height. A set of one or more velocimetric ultrasonic pulses may be generated and detected within the second flow portion. The flow velocity of the second pipeline fluid may be determined based on the generated set of velocimetric ultrasonic pulses and the detected set of velocimetric ultrasonic pulses.

A second ultrasonic absorption coefficient corresponding to a second pipeline fluid occupying a second flow portion of the multiflow pipeline may be determined. A second ultrasonic propagation factor corresponding to a second interface between the second pipeline fluid and a third pipeline fluid occupying a third flow portion of the pipeline may also be determined. An ultrasonic pulse may be generated and detected at a lowermost portion of a cross section of the pipeline and a second pipeline fluid film height may be calculated based on the generated ultrasonic pulse, the first ultrasonic absorption coefficient, the first ultrasonic propagation factor, the reflected ultrasonic pulse, the second ultrasonic absorption coefficient, the second ultrasonic propagation factor, and the second reflected ultrasonic pulse.

The cross sectional boundaries of the second flow portion may be determined based on the first and second pipeline fluid film heights. A set of one or more velocimetric ultrasonic pulses may be generated and detected within the cross sectional boundaries of the second flow portion. The flow velocity of the first pipeline fluid may be calculated based on the generated set of velocimetric ultrasonic pulses and the detected set of velocimetric ultrasonic pulses.

A location of the third cross sectional portion may be determined based on the first pipeline fluid film height and the second pipeline fluid film height. A set of one or more velocimetric ultrasonic pulses may be generated and detected within the cross sectional boundaries of the third flow portion, and the flow velocity of the first pipeline fluid may be calculated based on the generated set of velocimetric ultrasonic pulses and the detected set of velocimetric ultrasonic pulses.

In accordance with yet another embodiment of the present invention, a method of operating an ultrasonic measuring system is provided comprising the steps of: determining cross sectional boundaries of a flow portion of a multiflow pipeline; generating a set of one or more velocimetric ultrasonic pulses at at least one source point located within the cross sectional boundaries of the flow portion; detecting a set of one or more velocimetric ultrasonic pulses at at least one detection point located within the cross sectional boundaries of the flow portion; and calculating the flow velocity of the first pipeline fluid based on the generated set of velocimetric ultrasonic pulses and the detected set of velocimetric ultrasonic pulses.

Accordingly, it is an object of the present invention to provide a multiphase flow metering method and apparatus which enables non-intrusive, versatile, accurate, readily installable, and cost effective metering of distinct fluid phases within a multiphase fluid flow.

BRIEF DESCRIPTION OF THE SEVERAL VIEWS OF THE DRAWINGS

FIG. 1 is a schematic illustration of a process for determining fluid film heights in a two phase flow;

DETAILED DESCRIPTION OF THE INVENTION

Figure 1:
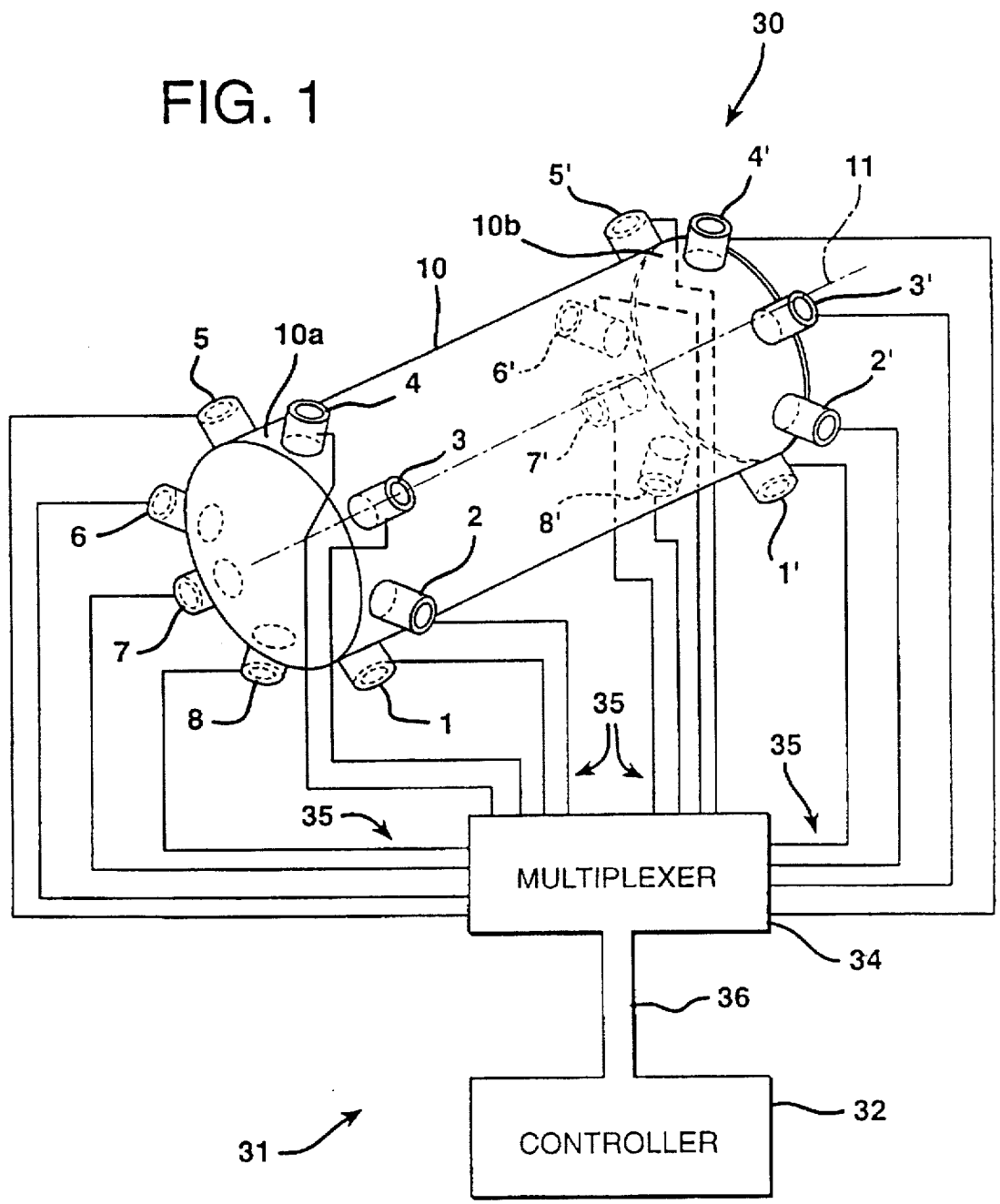
FIG. 1 is a schematic illustration of an apparatus for measuring a flow velocity of a fluid in a multiflow pipeline according to the present invention.

FIG. 1 illustrates an ultrasonic measuring system 30 according to the present invention. According to one embodiment of the present invention described herein, the ultrasonic measuring system 30 is utilized to determine a flow velocity of a selected fluid in a multiflow, pipeline 10 by generating and detecting velocimetric ultrasonic pulses in the selected fluid. According to another embodiment of the present invention described herein, the ultrasonic measuring system 30 is utilized to determine film heights of fluids flowing within the pipeline 10. It is contemplated by the present invention that a fluid may comprise a single phase material, e.g., a gas or a liquid, or a dual phase material, e.g., a liquid mist entrained in a gas flow.

The ultrasonic measuring system 30 includes a plurality of upstream ultrasonic transducers 1–8 and a plurality of downstream ultrasonic transducers 1'–8' coupled to the multiflow pipeline 10 so as to enable transmission of an ultrasonic signal through fluid within the pipeline 10. The upstream ultrasonic transducers 1–8 are positioned along a first cross sectional portion 10a of the pipeline 10 and the downstream ultrasonic transducers 1'–8' are positioned along a second cross sectional portion 10b of the pipeline 10. The first cross sectional portion 10a and the second cross sectional portion 10b are substantially perpendicular to the flow axis 11 of the pipeline 10. A detailed view of an appropriate transducer mount 40 is described herein with reference to FIGS. 5A and 5B.

A transducer control system 31 is coupled to the upstream and downstream ultrasonic transducers 1–8, 1'–8' and includes a programmable controller 32, preferably a personal computer including a digital microprocessing unit, and a signal multiplexer 34. The signal multiplexer 34 includes signal outputs 35 coupled to respective ones of the plurality of upstream and downstream ultrasonic transducers 1–8, 1'–8'. The controller 32 and the multiplexer 34 communicate via a digital data bus 36.

The transducer control system 31 is programmed so as to be operative to cause ultrasonic signals to be generated at one or more upstream or downstream ultrasonic transducers 1–8, 1'–8' and detected at one or more upstream or downstream ultrasonic transducers 1–8, 1'–8'. The particular transducer or transducers selected for generation and detection depends upon the requirements of the particular diagnostic application to be employed with the ultrasonic measuring system 30 of the present invention. For example, where the transducer control system 31 is programmed to determine the film height of a selected fluid within the multiflow pipeline or the film heights of each of a plurality of fluids present within the multiflow pipeline, at least one ultrasonic pulse is generated and detected in a single cross section of the pipeline 10, e.g., the first cross sectional portion 10a. Depending upon the diagnostic scheme established for determination of the film heights, the ultrasonic pulse may or may not be detected and generated at the same transducer. Specific diagnostic schemes for determining film heights of fluids within the pipeline 10 utilizing the ultrasonic measuring system 30 of the present invention are presented herein with reference to FIGS. 2 and 3.

Where the transducer control system 31 is programmed to determine a flow velocity of a single fluid selected from a plurality of fluids present within the multiflow pipeline 10, the transducer control system 31 is operative to generate and detect ultrasonic pulses within the single fluid. For example, according to the flow velocity determination scheme described below with reference to FIG. 4, the flow velocity of a single fluid selected from a plurality of fluids present within the multiflow pipeline 10 is determined by generating an ultrasonic pulse in the first cross sectional portion 10a and detecting the ultrasonic pulse in the second cross sectional portion 10b.

It is contemplated by the present invention that any number of upstream and downstream ultrasonic transducers 1–8, 1'–8' may be employed in the arrangement illustrated in FIG. 1. Specifically, if a more versatile or precise ultrasonic measuring system 30 is desired, more than eight upstream and downstream transducers 1–8, 1'–8' can be utilized. Conversely, if the level of versatility or precision represented by the number of transducers illustrated in FIG. 1 is beyond the needs of one practicing the present invention, a fewer number of transducers may be utilized.

Figure 2:
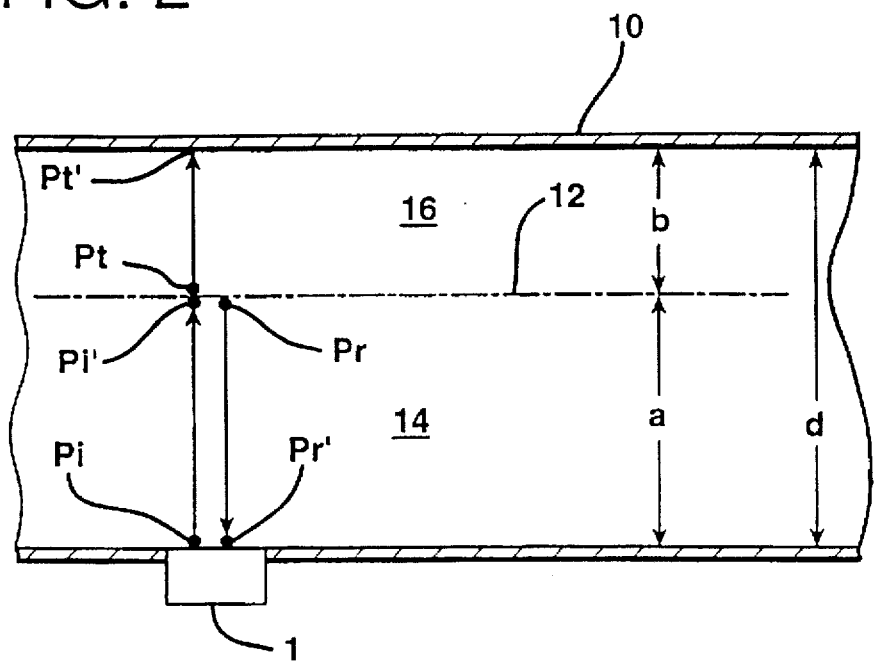
Figure 3:
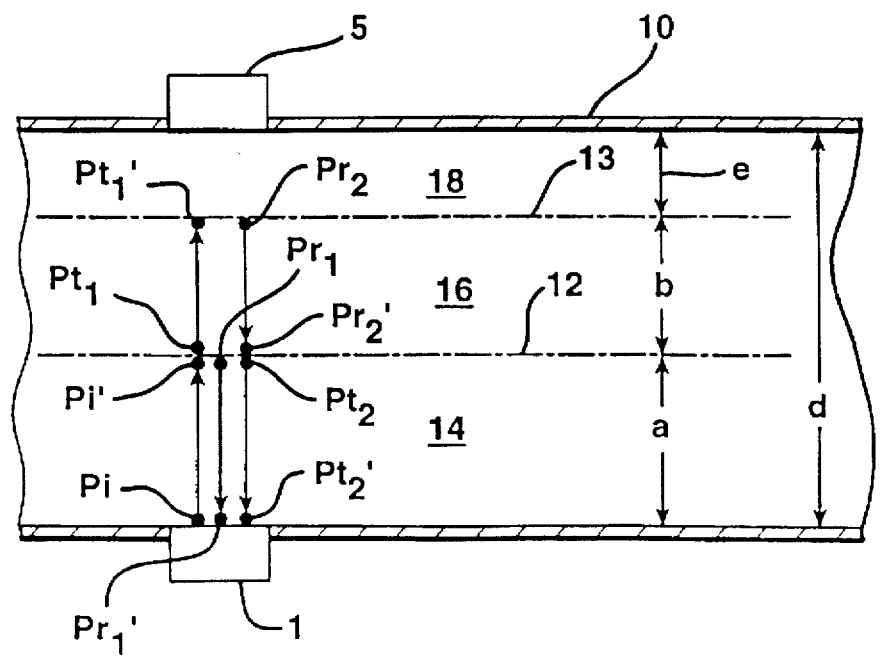
FIG. 3 is a schematic illustration of a process for determining fluid film heights in a three phase flow.

Referring now to FIGS. 2 and 3, where like elements are indicated with like reference numerals, a multiflow pipeline 10 and a diagnostic scheme for determining film heights of fluids flowing therein are illustrated. The pipeline 10 has a known inside diameter d and includes a first fluid medium 14 having a first fluid film height a, and a second fluid medium 16 having a second fluid film height b. A first fluid interface 12 defines the mutual boundary between the first medium 14 and the second medium 16. A lower or primary ultrasonic transducer 1 is coupled to a lowermost portion of a first cross section of the pipeline 10. The primary transducer 1 is capable of generating an ultrasonic pulse at the lowermost portion of the pipeline 10 and is also capable of detecting an ultrasonic pulse generated at the primary transducer 1 and reflected back to the primary transducer 1 or generated elsewhere and transmitted to the primary transducer 1. According to the present invention, the pulse generated by the primary transducer 1 is either a single ultrasonic pulse or a finite succession of ultrasonic pulses.

As a sound wave signal passes through a medium, its amplitude, i.e., pressure, decreases or is attenuated as follows:

$$P_x = P_0 e^{-\alpha x} \quad \text{equation (1)}$$

where $P_x$ is the pressure of the sound wave at a distance x from the source, $P_0$ is the pressure of the sound wave at the source, and $\alpha$ is the absorption coefficient of the medium. The absorption coefficient of the medium is related to its properties as follows:

$$\alpha = 2\pi f^2 \mu / (\rho c^3) \quad \text{equation (2)}$$

where f is the frequency of the sound wave, $\mu$ is the viscosity of the medium, $\rho$ is the density of the medium, and c is the velocity of sound in the medium.

An interface between two media may be characterized by a plurality of ultrasonic propagation factors including: (i) a first reflection factor for an ultrasonic wave incident on the interface from a first side of the interface; (ii) a second reflection factor for an ultrasonic wave incident on the interface from a second side of the interface; (iii) a first transmission factor for an ultrasonic wave incident on the interface from a first side of the interface; and (iv) a second transmission factor for an ultrasonic wave incident on the interface from a second side of the interface.

When an ultrasonic wave encounters an interface between two media at normal incidence, the wave energy is partially reflected and partially transmitted, as shown in FIG. 2. The ratio of the pressure of a reflected wave to an incident wave is defined as the reflection factor, R:

$$R = \{(\rho_1 c_1 - \rho_2 c_2)/(\rho_1 c_1 + \rho_2 c_2)\} \quad \text{equation (3)}$$

The ratio of the pressure of a transmitted wave to an incident wave is defined as the transmission factor, T:

$$T = \{2\rho_2 c_2 / (\rho_1 c_1 + \rho_2 c_2)\} \quad \text{equation (4)}$$

where $\rho_1$ is the density of the first medium, $c_1$ is the velocity of sound in the first medium, $\rho_2$ is the density of the second medium, and $c_2$ is the velocity of sound in the second medium.

An ultrasonic signal is generated at the primary transducer 1 and propagates through the pipeline 10 as illustrated in FIG. 2 according to the relationships defined in equations (1), (2), (3) and (4). $P_i$ is the pressure of the sound wave generated at the lowermost portion of the pipeline 10. $P_i'$ is the pressure of the sound wave after it passes through the first medium 14 and meets the first interface 12 between the first medium 14 and a second medium 16. Pt is the pressure of a sound wave transmitted through the first interface 12. $P_r$ is the pressure of a sound wave reflected from the first interface 12. $P_r'$ is the pressure of the reflected sound wave after it passes back through the first medium 14 and $P_t'$ is the pressure of the transmitted sound wave after it passes through the second medium 16.

The film height a of the first medium 14 and the film height b of the second medium 16 may be determined by generating the ultrasonic signal at the primary transducer 1 and detecting the ultrasonic signal reflected from the first interface 12. For the convenience of illustration, the quantity $e^{-\alpha x}$ corresponding to the attenuation of the sound wave by a medium, and as set forth in equation (1), will be identified herein as $P_\alpha$:

$$P_\alpha = e^{-\alpha x} \quad \text{equation (1a)}$$

Accordingly, $$P_i' = P_i(P_\alpha) \quad \text{equation (5)}$$

$$P_r' = P_r(P_\alpha); \; P_r = P_r'/(P_\alpha) \quad \text{equation (6)}$$

$P_i$ is a magnitude set in the primary transducer 1 and $P_r'$ is a magnitude detected at the primary transducer 1. The difference between $P_i$ and $P_r'$ is equal to the sum of the pressure $A_1$ absorbed in the first medium 14 between $P_i$ and $P_i'$, the pressure $A_2$ transmitted through the first interface 12, and the pressure $A_3$ absorbed in the first medium 14 between $P_r$ and $P_r'$:

$$P_i - P_r' = A_1 + A_2 + A_3. \quad \text{equation (7)}$$

$A_1$ can be expressed as follows:

$$A_1 = P_i - P_i'. \quad \text{equation (8)}$$

Equation (8) can be combined with equation (5):

$$A_1 = P_i - P_i(P_\alpha) = P_i(1 - P_\alpha). \quad \text{equation (9)}$$

$A_3$ can be expressed as follows:

$$A_3 = P_r - P_r'. \quad \text{equation (10)}$$

Equation (10) can be combined with equation (6):

$$A_3 = P_r'/(P_\alpha) - P_r'. \quad \text{equation (11)}$$

$A_2$ can be expressed in terms of an interface transmission factor, T, see equation (4), as follows:

$$A_2 = P_i'(T). \quad \text{equation (12)}$$

Equation (12) can be combined with equation (5):

$$A_2 = P_i(P_\alpha)(T). \quad \text{equation (13)}$$

Equations (9), (11), and (13) can be substituted into equation (7):

$$P_i - P_r' = P_i(1 - P_\alpha) + P_i(P_\alpha)(T) + P_r'/(P_\alpha) - P_r' \quad \text{equation (14)}$$

$$0 = -P_iP_\alpha + P_i(P_\alpha)(T) + P_r'/(P_\alpha)$$

$$0 = -P_iP_\alpha^2 + P_i(P_\alpha)^2(T) + P_r'$$

$$P_\alpha^2(P_i - P_i(T)) = P_r'$$

$$P_\alpha^2 = P_r'/P_i(1 - T)$$

$$P_\alpha = [P_r'/P_i(1 - T)]^{1/2}.$$

Equation (14) can be combined with equation (1a):

$$P_{\alpha 1} = [P_{r1}'/P_i(1-T)]^{1/2} = e^{-\alpha x} \quad \text{equation (15)}$$

where x is the film thickness, or film height a, of the first medium 14, α is determined using equation (2) or measured in a calibration system including a medium of interest with a known film height, $P_r'$ is measured at the primary transducer 1, and T is determined using equation (4) or measured in a calibration system including the mediums of interest. $P_i$ is proportional to the electrical volts applied to the primary transducer 1 and can be quantified by experimentally calibrating the transducer using a hydrophone within the pipeline 10 to account for pressure lost in the walls of the pipeline 10, as will be appreciated by those skilled in the art. Alternatively, $P_i$ can be quantified by experimentally calibrating the transducer using a hydrophone within a calibration system simulating the actual pipeline 10, as will be appreciated by those skilled in the art.

Accordingly, since x is the only unknown in equation (15), by generating and detecting an ultrasonic pulse at the primary transducer 1 and solving equation (15) for x, the film height a of the first medium 14 may be calculated. The film height a of the first medium 14 will be equal to x and may be confirmed by comparison with a film height determination derived from measuring the transit time of a sound wave reflected from the first interface 12. Specifically, the time required for the ultrasonic wave to travel from the primary transducer 1, through the first medium 14, be reflected at the first interface 12, and return back through the first medium 14 to the primary transducer 1 is defined as a first transit time t':

$$t' = (2a/c_{14}); \ a = (t'c_{14}/2) \quad \text{equation (16)}$$

where $c_{14}$, the velocity of sound in the first medium 14, is a quantity which can be measured experimentally or a known quantity which has been previously determined for the medium of interest.

The film height b of the second medium 16 is the difference between the film height a of the first medium 14 and the known inside diameter d of the pipeline 10:

$$b = d - a. \quad \text{equation (17)}$$

FIG. 3, illustrates a pipeline 10 having a known inside diameter d and including a first fluid medium 14, having a first fluid film height a, a second fluid medium 16, having a second fluid film height b, and a third fluid medium 18, having a third fluid film height e. A first fluid interface 12 defines the mutual boundary between the first medium 14 and the second medium 16. A second fluid interface 13 defines the mutual boundary between the second medium 16 and the third medium 18.

The film height a of the first medium 14 of FIG. 3 is determined in the same manner as the film height a of FIG. 2., with the understanding that equation (15) becomes:

$$P_{\alpha 1} = [P_{r1}'/P_i(1-T_1)]^{1/2} = e^{-\alpha_1 x} \quad \text{equation (15')}$$

where x is the film thickness, or film height a, of the first medium 14, α1, the absorption coefficient of the first medium 14, is determined in a calibration system including the first medium 14 with a known film height, $P_{r1}'$, the pressure of the sound wave after it passes back through the first medium 14, is measured at the primary transducer 1, and $T_1$, the transmission factor across the first interface when the wave is traveling from the first medium 14 to the second medium 16, is determined in a calibration system including the mediums of interest. Further, the film height a of the first medium 14 will be equal to x and may be confirmed by comparison with a film height determination derived from measuring the transit time of a sound wave reflected from the first interface 12 in the manner described above with reference to FIG. 2.

The film height b of the second medium 16 of FIG. 3 is determined from the measurement of $P_{r2}'$ at the primary transducer 1. $P_{r2}'$ can be expressed as follows:

$$P_{r2}' = P_{r2}(P_{\alpha 1}). \quad (18)$$

$P_{r2}$ can be expressed as follows:

$$P_{r2} = P_{r2}'(T_1') \quad (19)$$

where $T_1'$ is the transmission factor across the first interface 12 when the wave is traveling from the second medium 16 to the first medium 14. Equation (18) can be combined with equation (19):

$$P_{r2}' = P_{r2}'(T_1')(P_{\alpha 1}). \quad (20)$$

$P_{r2}'$ can be expressed as follows:

$$P_{r2}' = P_{r2}(P_{\alpha 2}). \quad (21)$$

Equation (20) can be combined with equation (21):

$$P_{r2}' = P_{r2}(P_{\alpha 2})(T_1')(P_{\alpha 1}). \quad (22)$$

$P_{r2}$ can be expressed as follows:

$$P_{r2} = P_{r1}'(R_2) = P_{r1}'(1-T_2) \quad (23)$$

where $R_2$ and $T_2$ are the reflection and transmission factors for a wave traveling from the second medium 16 to the third medium 18. Equation (22) can be combined with Equation (23):

$$P_{r2}' = P_{r1}'(1-T_2)(P_{\alpha 2})(T_1')(P_{\alpha 1}). \quad (24)$$

$P_{r1}'$ can be expressed as follows:

$$P_{r1}' = P_{r1}(P_{\alpha 2}). \quad (25)$$

Equation (24) can be combined with Equation (25):

$$P_{r2}' = P_{r1}(P_{\alpha 2})^2(1-T_2)(T_1')(P_{\alpha 1}) \quad (26)$$

$P_{r1}$ can be expressed as follows:

$$P_{r1} = P_i'(T_1) \quad (27)$$

where $T_1$ is the transmission factor across the first interface 12 when the wave is traveling from the first medium 14 to the second medium 16. Equation (26) can be combined with Equation (27):

$$P_{r2}' = P_i'(T_1)(P_{\alpha 2})^2(1-T_2)(T_1')(P_{\alpha 1}). \quad (28)$$

$P_i'$ can be expressed as follows:

$$P_i' = P_i(P_{\alpha 1}). \quad (29)$$

Equation (28) can be combined with Equation (29):

$$P_{r2}'=P_i(P_{o1})(T_1)(P_{o2})^2(1-t_2)(T_1')(P_{o1}) \qquad (30)$$

and rewritten as:

$$P_{o2}=[P_{r2}'/P_i(1-T_2)(P_{o1})^2(T_1)(T_1')]^{1/2}=e^{-\alpha_2 x} \qquad (31)$$

where x is the film thickness, or film height b, of the second medium 16, $\alpha 2$, the absorption coefficient of the second medium 14, is determined in a calibration system including the first medium 16 with a known film height, $P_{r1}'$, is measured at the primary transducer 1, and $T_1$ and $T_1'$ are determined in calibration systems including the respective mediums of interest.

Further, the film height b of the second medium 16 may be confirmed by comparison with a film height determination derived from measuring the transit times of respective sound waves reflected from the first interface 12 and the second interface 13. Specifically, the film height a of the first medium 14 may be confirmed by comparison with a film height determination derived from measuring the transit time of a sound wave reflected from the first interface 12 in the manner described above with reference to FIG. 2. The film height b of the second medium 16 may be confirmed by noting the film height a of the first medium 14 and the time required for the ultrasonic wave to travel from the primary transducer 1, through the first medium 14 and the second medium 16, be reflected at the first interface 12 and the second interface 13, and return back through the first medium 14 and the second medium 16 to the primary transducer 1. The second transit time t" is thus defined as:

$$T''=t'+(2b/c_{16}); b=[c_{16}(t''-t')/2] \qquad \text{equation (32)}$$

where $c_{16}$, the velocity of sound in the second medium 16, is a quantity which can be measured experimentally or a known quantity which has been previously determined for the medium of interest.

The film height e of the third medium 18 is determined according to the following equation:

$$e=d-a-b \qquad \text{equation (33)}$$

where d, the inside diameter of the pipeline 10, is a known value.

Figure 4:
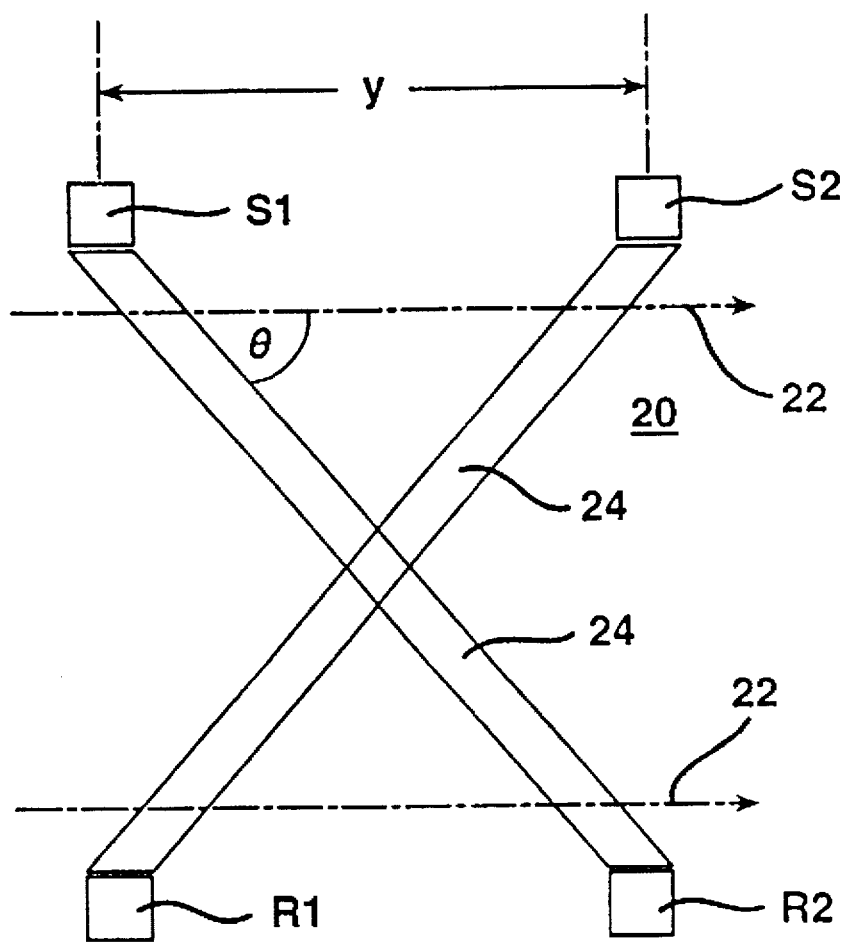
FIG. 4 is a schematic illustration of a process of measuring the flow velocity of a selected fluid layer.

Referring now to FIG. 4, where like elements are indicated with like reference numerals, a diagnostic scheme for determining the flow velocity of a selected fluid layer 20, flowing in the direction indicated generally by arrows 22, is illustrated. First, the cross sectional boundaries of each flow portion are determined from either the inside pipe diameter d and the fluid film heights a and b or the inside pipe diameter d and the fluid film heights a, b, and e, depending upon the number of flow portions, i.e. fluid phases, within the pipeline 10. The inside pipe diameter d is a known value and the fluid film heights a, b, and e may either be known values or may be determined according to the fluid film height determination scheme described herein with reference to FIGS. 2 and 3. The fluid film heights a, b, and e, are used to determine the boundaries of the distinct flow portions within the pipeline 10.

To determine the flow velocity of the selected fluid layer 20, velocimetric ultrasonic signals, represented schematically by paths 24, are generated and detected within a selected one of the plurality of flow portions. An ultrasonic measuring system 30 for generating velocimetric ultrasonic signals within a single selected fluid layer is described herein in detail with reference to FIG. 1.

Flow velocity can be determined using velocimetric pulses within the selected fluid layer 20 in a variety of diagnostic schemes. For example, according to one diagnostic scheme, velocimetric pulses are utilized to determine fluid velocity by measuring the change in transit time for a sound wave to travel in opposite directions between two points in a moving fluid. Specifically, as is illustrated in FIG. 4, a first pair of transducers include a generating transducer S1 and a detecting transducer R2 positioned within the selected fluid and a second pair of transducers include a generating transducer S2 and a detecting transducer R1. The transducers S1, S2, R1, R2 are positioned in the selected fluid layer 20 and are separated along the axis of flow by a known distance y. Velocimetric pulses are generated simultaneously at the first and second generating transducers S1, S2 and subsequently detected at the first and second detecting transducers R1, R2. The time interval $t_1$ for the signal to travel in the upstream direction, i.e., from S2 to R1, and the time interval $t_2$ for the signal to travel in the downstream direction, i.e., from S1 to R2, are noted. The difference $\Delta t$ between $t_1$ and $t_2$ can be related to the moving fluid as follows:

$$\Delta t=(2V_f y \cos \theta)/c^2 \qquad \text{equation (34)}$$

where $V_f$ is the fluid velocity, y is the distance between the upstream and downstream transducers, $\theta$ is the angle of inclination, with respect to the fluid flow direction, of the paths defined between the generating and detecting transducers, and c is the velocity of sound in the medium of interest. Where $V_f$ is the only unknown, the equation is solved to determine the fluid velocity $V_f$.

It should be noted that, for illustrative purposes, the paths 24 represent only a portion of the actual ultrasonic signal generated at the transducers S1, S2. The actual ultrasonic signal generated at the transducers S1, S2 is substantially in the form of an ultrasonic wave originating at a point source and diverging radially outward therefrom. It is contemplated by the present invention that the ultrasonic signals generated at the transducers S1, S2 may represent any one of a variety of signal distributions, orientations, magnitudes, velocities, frequencies, etc., so long as the signal selected is one that will travel through the medium of interest and be detected at a corresponding transducer.

In the event the medium of interest comprises a dual phase material, e.g., a liquid mist entrained in a gas flow, it is noted that equation (2) can be used to determine the apparent density of the medium. The respective quantities of each material forming the dual phase flow can be determined from the apparent density of the medium.

Figure 5B:
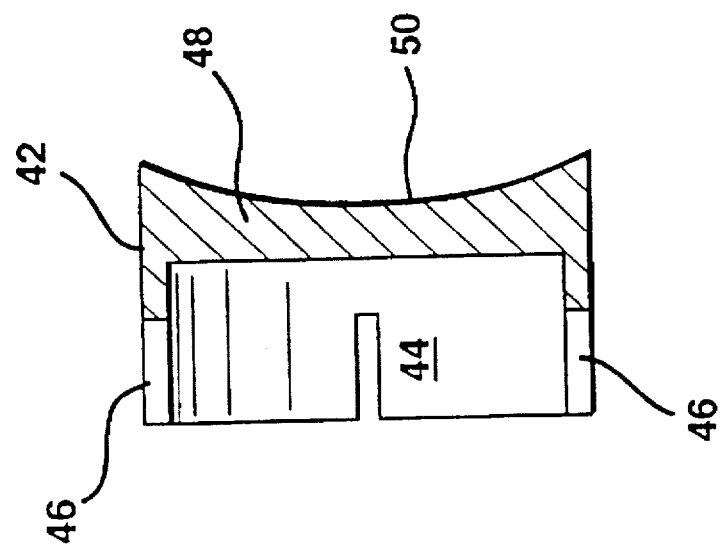
FIG. 5B is a plan view, taken along line 5B—5B of FIG. 5A, of a transducer mount according to the present invention.
Figure 5A:
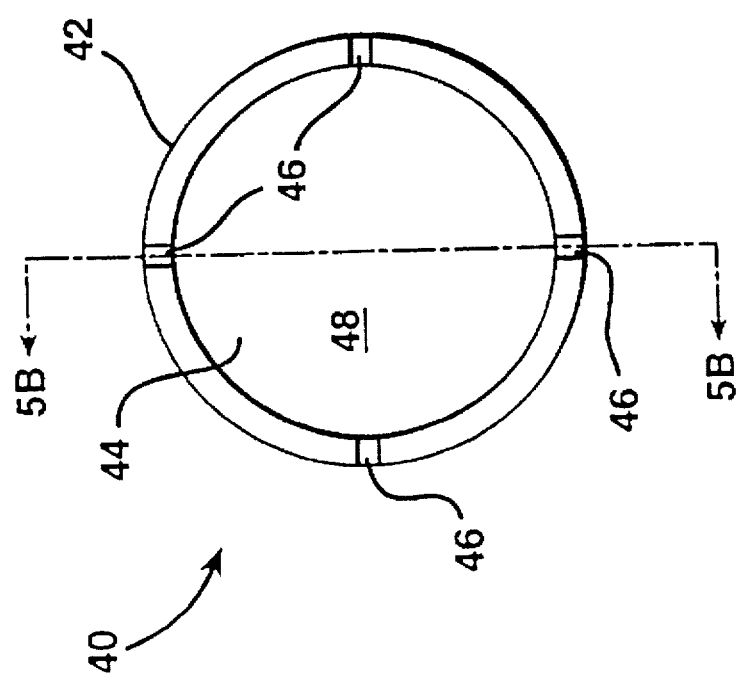
FIG. 5A is a plan view of a transducer mount according to the present invention.

Referring now to FIGS. 5A and 5B, a transducer mount 40 is illustrated. The mount 40 includes a substantially circular support portion 42 which defines a transducer receiving cavity 44 therein. The diameter of the support portion 42 is selected so as to form a close fit with a transducer inserted into the cavity 44. A plurality of saw cuts 46 are provided in the support portion 42 to enable the support portion to yield slightly and maintain a friction fit as a transducer is inserted into the cavity 44.

The transducer mount 40 also includes a pipe engaging portion 48 which, in turn, includes a contoured portion 50. The transducer mount is welded or otherwise fastened to a pipeline (not shown) such that the contoured portion engages the outer surface of the pipeline and follows the contour of the outer surface of the pipeline. For example, where the transducer mount 40 is to be coupled to a pipeline of circular cross section, the radius of curvature of the contoured portion 50 is substantially equal to the radius of curvature of the outer surface of the pipeline.

In one embodiment of the present invention, the transducer mount 40 defines a 0.25" (0.64 cm) thick stainless steel body extending a maximum of approximately 1.25" (3.2 cm) from the contoured portion 50 to the opposite end of the mount 40. The saw cuts 46 are 0.5" (1.27 cm) deep. The cavity 44 defines a 1.75" (4.44 cm) inside diameter and is approximately 0.75" (1.92 cm) deep.

Having described the invention in detail and by reference to preferred embodiments thereof, it will be apparent that modifications and variations are possible without departing from the scope of the invention defined in the appended claims. For example, it is contemplated by the present invention that the values and variables determined according to the present invention may be determined through an estimation, a calculation, a measurement, or otherwise. Further, it should be understood that, for the purpose of the present specification and claims, a value or variable which is indicated to be determined is a value or variable which is estimated, a calculated, or measured.

The invention claimed is:

1. An ultrasonic measuring system comprising:
   a plurality of upstream ultrasonic transducers coupled to a multiflow pipeline and positioned along a first cross sectional portion of a multiflow pipeline;
   a plurality of downstream ultrasonic transducers coupled to a multiflow pipeline and positioned along a second cross sectional portion of said multiflow pipeline; and
   a transducer control system coupled to said plurality of upstream ultrasonic transducers and said plurality of downstream ultrasonic transducers, wherein said transducer control system is operative to determine a flow velocity of a single fluid selected from a plurality of fluids present within said multiflow pipeline by generating an ultrasonic pulse in a first cross section of said pipeline and detecting said ultrasonic pulse in another cross section of said pipeline.

2. An ultrasonic measuring system as claimed in claim 1 wherein said first cross sectional portion is substantially perpendicular to a flow axis of said pipeline and wherein said second cross sectional portion is substantially perpendicular to said flow axis of said pipeline.

3. An ultrasonic measuring system claimed in claim 1 wherein said transducer control system comprises a programmable controller and a signal multiplexer and wherein said signal multiplexer includes signal outputs coupled to respective ones of said plurality of upstream and downstream ultrasonic transducers.

4. An ultrasonic measuring system as claimed in claim 1 wherein said transducer control system is operative to cause ultrasonic signals to be generated at one of said plurality of upstream and downstream ultrasonic transducers and detected at another of said plurality of upstream and downstream ultrasonic transducers.

5. An ultrasonic measuring system as claimed in claim 1 wherein said transducer control system is operative to cause ultrasonic signals to be generated at any one of said plurality of upstream and downstream ultrasonic transducers and detected at any one of said plurality of upstream and downstream ultrasonic transducers.

6. An ultrasonic measuring system as claimed in claim 1 wherein said transducer control system is operative to determine a film height of a selected fluid within said multiflow pipeline.

7. An ultrasonic measuring system as claimed in claim 1 wherein said transducer control system is further operative to determine film heights of each of a plurality of fluids present within said multiflow pipeline by generating and detecting at least one ultrasonic pulse in a single cross section of said pipeline.

8. An ultrasonic measuring system as claimed in claim 6 wherein said transducer control system is operative to determine said film height of said selected fluid by causing ultrasonic signals to be generated and detected at a lowermost portion of a single cross section of said multiflow pipeline.

9. An ultrasonic measuring system as claimed in claim 8 wherein first and second reflected ultrasonic signals are detected at said lowermost portion.

10. An ultrasonic measuring system as claimed in claim 1 wherein said transducer control system is operative to generate and detect ultrasonic pulses within a single fluid selected from a plurality of fluids present within said multiflow pipeline.

11. An ultrasonic measuring system as claimed in claim 1 wherein said transducer control system is operative to determine a flow velocity of a single fluid selected from a plurality of fluids present within said multiflow pipeline by generating and detecting ultrasonic pulses within said single fluid.

12. A method of operating an ultrasonic measuring system comprising the steps of:
   determining a first ultrasonic absorption coefficient corresponding to a first pipeline fluid occupying a first flow portion of a multiflow pipeline;
   determining a first ultrasonic propagation factor corresponding to a first interface between said first pipeline fluid and a second pipeline fluid occupying a second flow portion of the pipeline;
   generating an ultrasonic pulse at a lowermost portion of a cross section of the pipeline;
   detecting a first reflected ultrasonic pulse at said lowermost portion, said first reflected ultrasonic pulse being reflected from said interface between said first pipeline fluid and said second pipeline fluid; and
   calculating a first pipeline fluid film height based on the generated ultrasonic pulse, the first ultrasonic absorption coefficient, said first ultrasonic propagation factor, and the first reflected ultrasonic pulse.

13. A method of operating an ultrasonic measuring system as claimed in claim 12 further comprising the steps of:
   determining cross sectional boundaries of said first flow portion based on the first pipeline fluid film height;
   generating a set of one or more velocimetric ultrasonic pulses at at least one source point located within said cross sectional boundaries of said first flow portion;
   detecting a set of one or more velocimetric ultrasonic pulses at at least one detection point located within said cross sectional boundaries of said first flow portion; and
   calculating the flow velocity of said first pipeline fluid based on the generated set of velocimetric ultrasonic pulses and the detected set of velocimetric ultrasonic pulses.

14. A method of operating an ultrasonic measuring system as claimed in claim 12 further comprising the steps of:
   determining cross sectional boundaries of said second flow portion based on the first pipeline fluid film height;
   generating a set of one or more velocimetric ultrasonic pulses at at least one source point located within said second flow portion;
   detecting a set of one or more velocimetric ultrasonic pulses at a detection point located within said second flow portion; and calculating the flow velocity of said second pipeline fluid based on the generated set of velocimetric ultrasonic pulses and the detected set of velocimetric ultrasonic pulses.

15. A method of operating an ultrasonic measuring system as claimed in claim 12 further comprising the steps of:

determining a second ultrasonic absorption coefficient corresponding to a second pipeline fluid occupying a second flow portion of said multiflow pipeline;

determining a second ultrasonic propagation factor corresponding to a second interface between said second pipeline fluid and a third pipeline fluid occupying a third flow portion of the pipeline;

generating an ultrasonic pulse at a lowermost portion of a cross section of said pipeline;

detecting a second reflected ultrasonic pulse at said lowermost portion, said second reflected ultrasonic pulse being reflected from said interface between said second pipeline fluid and said third pipeline fluid; and calculating a second pipeline fluid film height based on the generated ultrasonic pulse, the first ultrasonic absorption coefficient, said first ultrasonic propagation factor, the reflected ultrasonic pulse, the second ultrasonic absorption coefficient, said second ultrasonic propagation factor, and the second reflected ultrasonic pulse.

16. A method of operating an ultrasonic measuring system as claimed in claim 15 further comprising the steps of:

determining cross sectional boundaries of said second flow portion based on the first and second pipeline fluid film heights;

generating a set of one or more velocimetric ultrasonic pulses at at least one source point located within said cross sectional boundaries of said second flow portion;

detecting a set of one or more velocimetric ultrasonic pulses at at least one detection point located within said cross sectional boundaries of said second flow portion; and calculating the flow velocity of said first pipeline fluid based on the generated set of velocimetric ultrasonic pulses and the detected set of velocimetric ultrasonic pulses.

17. A method of operating an ultrasonic measuring system as claimed in claim 15 further comprising the steps of:

determining a location of said third cross sectional portion based on the first pipeline fluid film height and the second pipeline fluid film height;

generating a set of one or more velocimetric ultrasonic pulses at at least one source point located within said cross sectional boundaries of said third flow portion;

detecting a set of one or more velocimetric ultrasonic pulses at at least one detection point located within said cross sectional boundaries of said third flow portion; and calculating the flow velocity of said first pipeline fluid based on the generated set of velocimetric ultrasonic pulses and the detected set of velocimetric ultrasonic pulses.

18. A method of operating an ultrasonic measuring system as claimed in claim 12 wherein at least one of said first pipeline fluid and said second pipeline fluid is a dual phase material.

19. A method of determining a flow velocity of a single fluid selected from a plurality of fluids present within a multiflow pipeline, said method comprising the steps of:

generating an ultrasonic pulse at a selected one of a plurality of upstream ultrasonic transducers coupled to said multiflow pipeline along a first cross sectional portion of said multiflow pipeline; and detecting said ultrasonic pulse at a selected one of a plurality of downstream ultrasonic transducers coupled to said multiflow pipeline along a second cross sectional portion of said multiflow pipeline, wherein said selected upstream ultrasonic transducer and said selected downstream ultrasonic transducer are positioned within said single fluid.

* * * * *

REEXAMINATION CERTIFICATE (3936th)

United States Patent [19]
Jepson et al.

[11] B1 5,719,329
[45] Certificate Issued Nov. 16, 1999

[54] ULTRASONIC MEASURING SYSTEM AND METHOD OF OPERATION

[75] Inventors: William Paul Jepson; Madan Gopal, both of Athens, Ohio

[73] Assignee: Ohio University, Athens, Ohio

Reexamination Request:
No. 90/004,978, Apr. 28, 1998

Reexamination Certificate for:
Patent No.: 5,719,329
Issued: Feb. 17, 1998
Appl. No.: 08/768,994
Filed: Dec. 18, 1996

Related U.S. Application Data

[60] Provisional application No. 60/009,288, Dec. 28, 1995.
[51] Int. Cl.⁶ .......................... G01N 29/02; G01N 29/28; G01F 1/74
[52] U.S. Cl. .......................... 73/61.49; 73/597; 73/861.04
[58] Field of Search .................................. 73/597, 19.03, 73/54.41, 61.49, 861.04, 861.18, 861.25–861.31

[56] References Cited

U.S. PATENT DOCUMENTS 4,162,630   7/1979   Johnson .................................. 73/194 A

*Primary Examiner*—Hezron E. Williams

[57] ABSTRACT

An ultrasonic measuring system is provided including a plurality of upstream and downstream ultrasonic transducers coupled to a multiflow pipeline and positioned along first and second cross sectional portions of the multiflow pipeline. A transducer control system is coupled to the upstream and downstream ultrasonic transducers for selective activation of the transducers. In one embodiment, the ultrasonic measuring system is ultilized to determine a flow velocity of a selected fluid in a multiflow pipeline by generating and detecting velocimetric ultrasonic pulses in the selected fluid. In another embodiment, the ultrasonic measuring system is utilized to determined film heights of fluids flowing within the pipeline.

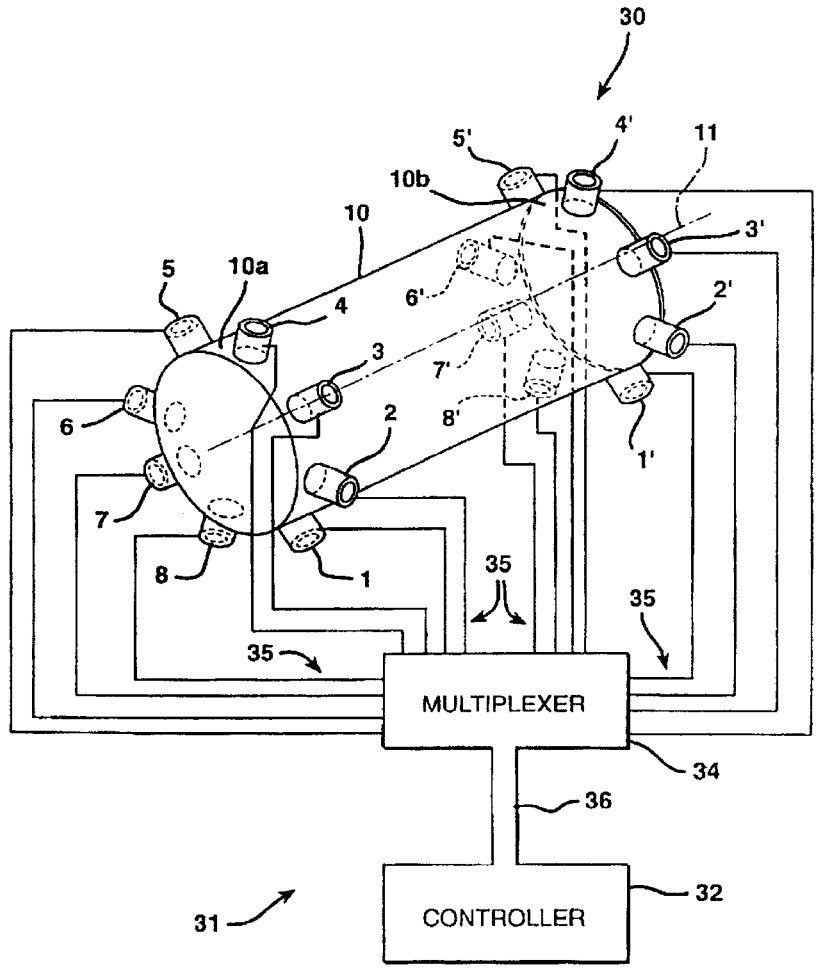

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *